US010405930B2

(12) United States Patent
Richmond et al.

(10) Patent No.: US 10,405,930 B2
(45) Date of Patent: Sep. 10, 2019

(54) SYSTEM FOR SENSING TISSUE DEFORMATION

(71) Applicant: SYNAPTIVE MEDICAL (BARBADOS) INC., Bridgetown (BB)

(72) Inventors: Joshua Lee Richmond, Toronto (CA); Cameron Anthony Piron, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/890,621

(22) Filed: Feb. 7, 2018

(65) Prior Publication Data

US 2018/0161107 A1    Jun. 14, 2018

Related U.S. Application Data

(63) Continuation of application No. 15/129,674, filed as application No. PCT/IB2016/051432 on Mar. 13, 2016, now Pat. No. 9,918,799.

(51) Int. Cl.
| | |
|---|---|
| *A61B 5/00* | (2006.01) |
| *A61B 34/20* | (2016.01) |
| *A61B 5/01* | (2006.01) |
| *G01B 11/16* | (2006.01) |
| *G01B 7/16* | (2006.01) |
| *A61B 5/053* | (2006.01) |
| *A61B 5/06* | (2006.01) |

(52) U.S. Cl.
CPC ............ *A61B 34/20* (2016.02); *A61B 5/0084* (2013.01); *A61B 5/01* (2013.01); *A61B 5/053* (2013.01); *A61B 5/064* (2013.01); *A61B 5/6847* (2013.01); *A61B 5/742* (2013.01); *G01B 7/16* (2013.01); *G01B 11/165* (2013.01); *G01B 11/18* (2013.01); *A61B 5/0013* (2013.01); *A61B 5/7425* (2013.01); *A61B 5/7475* (2013.01); *A61B 2034/2061* (2016.02); *A61B 2562/0261* (2013.01)

(58) Field of Classification Search
CPC ............ A61B 2562/0261; A61B 34/20; A61B 5/0013; A61B 5/0084; A61B 5/01; A61B 5/053; A61B 5/064; A61B 5/6847; A61B 5/742; A61B 5/7425; A61B 5/7475; G01B 11/165; G01B 11/18; G01B 7/16
See application file for complete search history.

(56) References Cited

U.S. PATENT DOCUMENTS

| | | |
|---|---|---|
| 6,718,196 B1 | 6/2004 | Mah |
| 2007/0156019 A1 | 7/2007 | Larkin et al. |
| 2011/0034981 A1 | 2/2011 | Schulte et al. |
| 2013/0303893 A1 | 11/2013 | Duindam |
| 2013/0345718 A1 | 12/2013 | Crawford et al. |
| 2015/0100064 A1 | 4/2015 | Skakoon et al. |
| 2015/0272698 A1 | 10/2015 | Rolfes et al. |

FOREIGN PATENT DOCUMENTS

WO    2013025678 A1    2/2013

*Primary Examiner* — Ruth S Smith
(74) *Attorney, Agent, or Firm* — Perry + Currier Inc.

(57) ABSTRACT

The present invention provides a device and method for measuring tissue deformation during an invasive medical procedure. A device is provided comprising a flexible fiber having a proximal end and a distal end; at least one sensor embedded in the flexible fiber; a rigid mount having a transverse opening for the flexible fiber; a mechanism for inserting the flexible fiber into a tissue; a detector for receiving information from the sensor; and a tracking system for receiving information from the detector to calculate the sensor location.

16 Claims, 12 Drawing Sheets

SYSTEM FOR SENSING TISSUE DEFORMATION

FIELD

The present disclosure relates to navigation systems and methods for minimally invasive therapy, and more specifically to a device and methods for sensing tissue deformation during medical procedures.

BACKGROUND

Surgical procedures have been greatly assisted by the implementation of navigation systems. Navigation systems assist in surgery by providing previously acquired imaging information, such as magnetic resonance imaging (MRI), during surgery to visualize tissue morphology and locate target areas. Navigation systems may also be used to track surgical instruments and their location within the tissue during surgery, typically incorporating information from previously acquired imaging data. As an example, minimally invasive brain surgery may incorporate navigation systems to map a target area for surgical resection and access the target area with minimal damage to healthy brain tissue.

Surgical procedures that exert pressure on tissues and organs or alter their composition may produce deformation of tissue. For example, deformation of brain tissue may occur when a craniotomy is opened and pressure on the brain is relieved, when a surgical device such as a surgical port or catheter is introduced into the brain, or when tissue is removed during surgery such as in a tumour resection. The tissue deformation may render the surgical plan based on pre-operative imaging inaccurate and reduce the usefulness of the image-guided therapy. Deformation of tissue and its effects on the accuracy and precision of surgical procedures is an ongoing area of investigation and research, and there is a need for effective means to detect such deformation for surgical planning, navigation, and analysis. While much of the following discussion relates to surgical procedures in the brain as examples, similar issues arise in surgery to the spine and other orthopedic applications and the techniques are generally applicable.

The complexities associated with tissue shifts that occur during surgery are not well addressed by currently available systems and methods. For example during a craniotomy, when a large portion of the skull of a patient is removed to allow for access to the brain, the brain tends to swell outside of the remaining skull that is encasing the brain due to a pressure differential between the brain and the operating room. This brain swelling, and brain sag due to gravity, may lead to a significant shift in the brain tissue, often on the order of 1-2 cm. Additionally, as a tumor is resected from the brain, the position of the remaining tissue may shift relative to the pre-operative images as a result of the decreased volume. These mechanisms of brain swelling, sag, and shift may result in significant variations between pre-operative and intra-operative brain positions.

Thus, there is a need for effective means to detect tissue deformation resulting from various causes including tissue resection, swelling, and surgical tool insertions, to accommodate those changes and to allow for improved surgical planning, navigation, and analysis.

SUMMARY

A further understanding of the functional and advantageous aspects of the disclosure can be realized by reference to the following detailed description and drawings.

An object of the present invention is to provide devices and methods for measuring tissue deformation during invasive therapy. A further object of the present invention is to provide devices and methods to reduce tissue deformation during invasive therapy.

Thus by one broad aspect of the present invention, a device is provided comprising a flexible fiber having a proximal end and a distal end; at least one sensor embedded in the flexible fiber; a rigid mount having a transverse opening for the flexible fiber; a mechanism for inserting the flexible fiber into a tissue; a detector for receiving information from the sensor; and a tracking system for receiving information from the detector to calculate the sensor location.

By another broad aspect of the present invention, a method is provided for sensing tissue deformation intraoperatively comprising reversibly affixing at least one rigid mount to a bone overlying a tissue; measuring the rigid mount location using a tracking system; inserting a flexible fiber with at least one embedded sensor through a transverse opening in the rigid mount and the bone into the tissue using an insertion mechanism; receiving a signal from the sensor by a detector; calculating the sensor location using the signal and the rigid mount location; and calculating the tissue deformation using the sensor location.

BRIEF DESCRIPTION OF THE DRAWINGS

Embodiments will now be described, by way of example only, with reference to the drawings, in which:

FIG. 10 (b) is a diagram showing a generic strain detection feedback systems function.

FIG. 10 (c) is a diagram showing a wavelength multiplexed strain detection feedback system.

FIG. 10 (d) is a diagram showing an intensity division multiplexed strain detection feedback system.

FIG. 10 (e) is a diagram showing two OTDR based strain detection feedback systems.

FIG. 11 (b) is a diagram showing a spatially division multiplexed strain detection feedback system.

FIG. 11 (c) is a diagram showing an electrical strain detection feedback system.

FIG. 12 (b) is an illustration of a combined multiplexing system of fiber Bragg grating sensors and electrical sensors.

DETAILED DESCRIPTION

Figure 1:
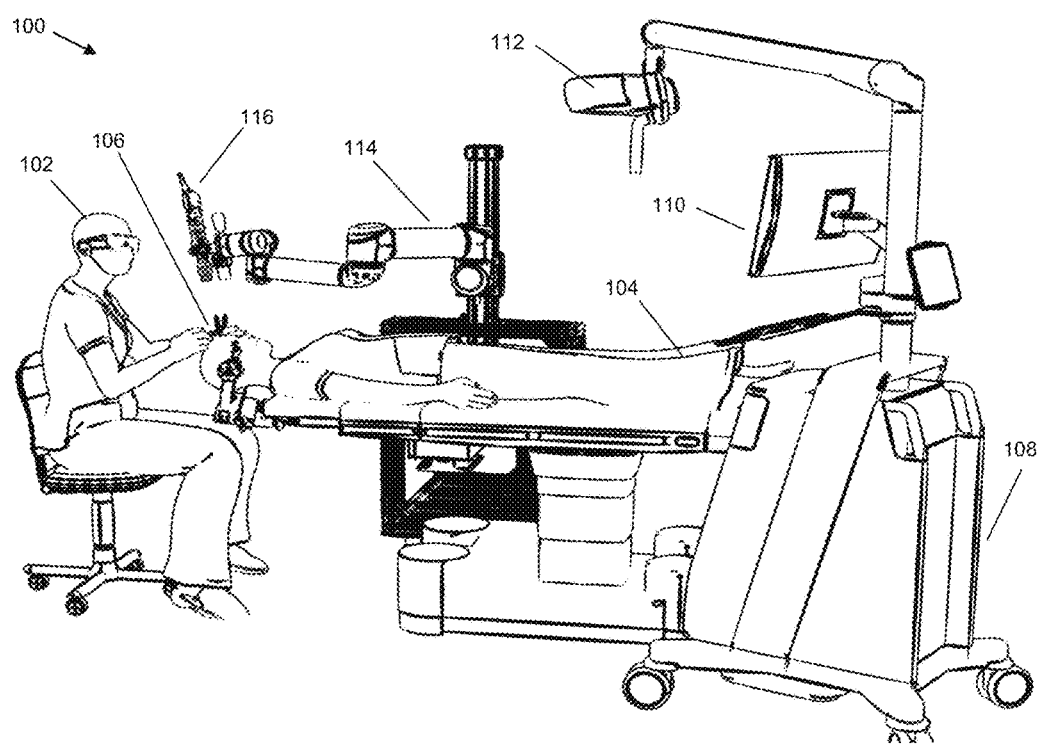
FIG. 1 depicts an operating theatre, according to a non-limiting embodiment.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. The section headings used herein are for organizational purposes only and are not to be construed as limiting the subject matter described.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port. An example of an access port is an intracranial access port which may be employed in neurological procedures in order to provide access to internal tissue pathologies, such as tumors.

FIG. 1 depicts a surgical operating theatre 100 in which a healthcare worker 102 (e.g. a surgeon) operates on a patient 104. Specifically, surgeon 102 is shown conducting a minimally invasive surgical procedure on the brain of patient 104. The description below makes reference to the brain of patient 104 as an example of tissue to which the techniques herein may be applied. It will be understood, however, that those techniques may also be applied to a wide variety of other tissues. Thus, when the brain of patient 104 is mentioned below, it is simply an example of the various tissues in connection with which the systems and methods herein may be implemented.

The opening through which surgeon 102 inserts and manipulates instruments is provided by an access port 106. Following insertion of access port 106, the access port may enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as one or more displays 110 connected to the computing device for displaying images provided by the computing device.

Equipment tower 108 also supports a tracking system 112. Tracking system 112 is generally configured to track the positions of one or more markers, for example reflective markers, (not shown) mounted on any of the above-mentioned surgical tools, or any combination thereof. Tracking system 112 may therefore include a camera (e.g. a stereo camera) and a computing device (either the same device as mentioned above or a separate device) configured to locate the markers in the images captured by the camera, and determine the spatial positions of those markers within the operating theatre. The spatial positions may be provided by tracking system 112 to the computing device in equipment tower 108 for subsequent use.

Also shown in FIG. 1 is an automated articulated arm 114, also referred to as a robotic arm, carrying an external scope 116 (i.e. external to patient 104). External scope 116 may be positioned over the surgical field by robotic arm 114, and may capture images of the brain of patient 104 for presentation on display 110. The movement of robotic arm 114 to place external scope 116 correctly over the surgical area may be guided by tracking system 112 and the computing device in equipment tower 108. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images may be collected of patient 104, or at least of the brain of patient 104 or portions thereof. Preoperative images may be used for planning purposes. Examples of planning activities include marking, in the preoperative images, the location of a target portion of patient tissue. Such a target portion may include a tumor to be resected, for example. The computing device housed in equipment tower 108 can perform various actions to employ the preoperative images and evaluate the accuracy of a resection procedure, in comparison with the planned resection.

Figure 2:
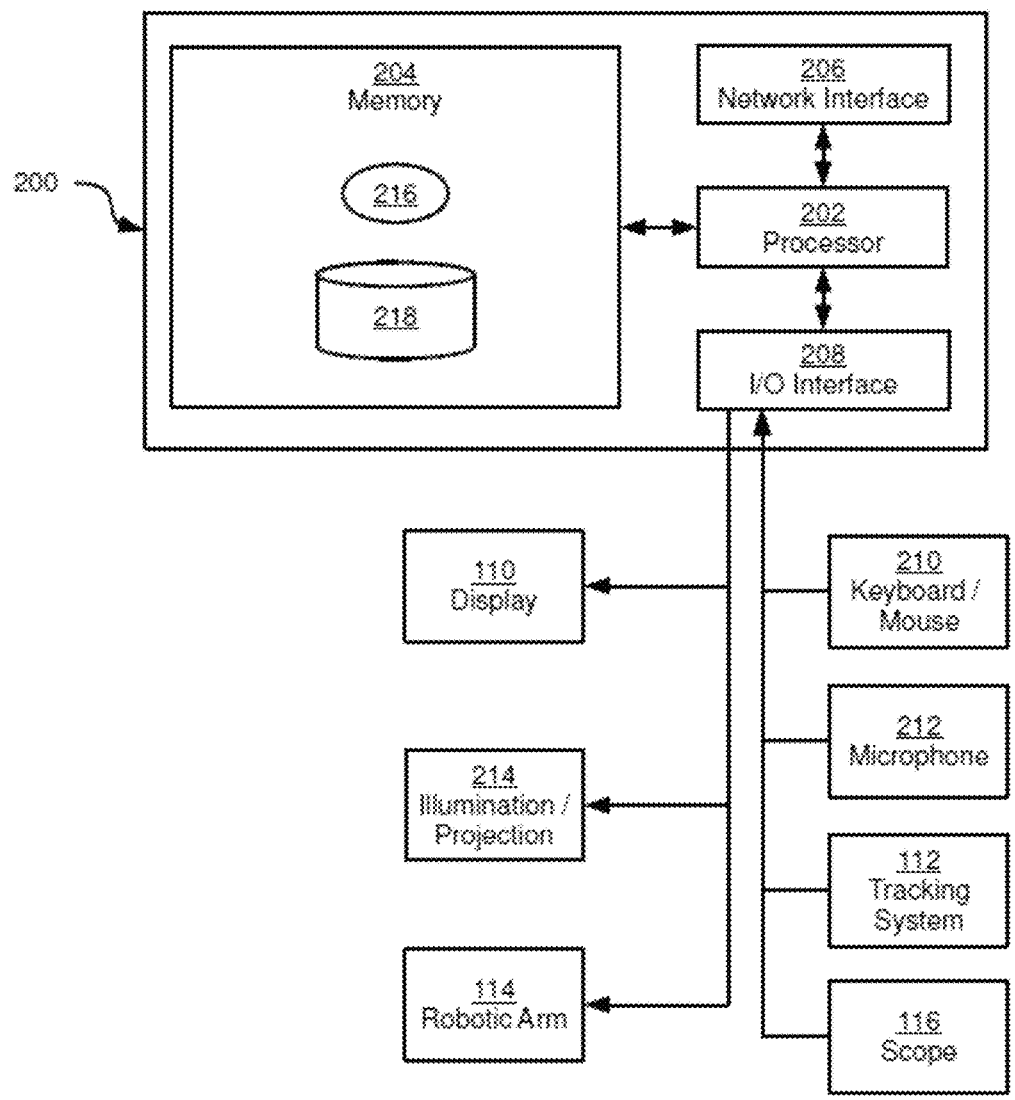
FIG. 2 depicts a computing device of the operating theatre of FIG. 1, according to a non-limiting, embodiment.

A brief description of the components of the computing device will be provided here. Referring to FIG. 2, a computing device 200 is depicted, including a central processing unit (also referred to as a microprocessor or simply a processor) 202 interconnected with a non-transitory computer readable storage medium such as a memory 204. Computing device 200 also includes a network interface 206 interconnected with processor 202. Network interface 206 allows computing device 200 to communicate with other computing devices via a network (e.g. a local area network (LAN), a wide area network (WAN) or any suitable combination thereof).

Computing device 200 also includes an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to input devices including a keyboard and mouse 210, a microphone 212, as well as scope 116 and tracking system 112, mentioned above. Also via interface 208, computing device 200 is connected to output devices including illumination or projection components 214 (e.g. lights, projectors and the like), as well as display 110 and robotic arm 114 mentioned above. Other input (e.g. touch screens) and output devices (e.g. speakers) will also occur to those skilled in the art.

Computing device 200 stores, in memory 204, a resection evaluation application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, Processor 202, or computing device 200 more generally, is therefore said to be "configured" or "operating" to perform those functions via the execution of application 216.

Also stored in memory 204 are various data repositories, including a patient data repository 218. Patient data repository can contain surgical planning data, preoperative and intraoperative images, and the like.

As described above, pre-operative and intraoperative images provide surgical planning data that may be utilized to guide placement of surgical instruments and to determine the location of the tissue to be surgically manipulated or resected. For example, the location of target tissue to be resected is mapped on preoperative images and stored in computing device 200. However, surgical manipulations such as opening of the skull and insertion of medical instruments can alter and deform the tissue, such that the surgical planning data becomes inaccurate. To address this problem and compensate for such tissue deformations, a deformation sensor device is provided as described below.

Figure 3:
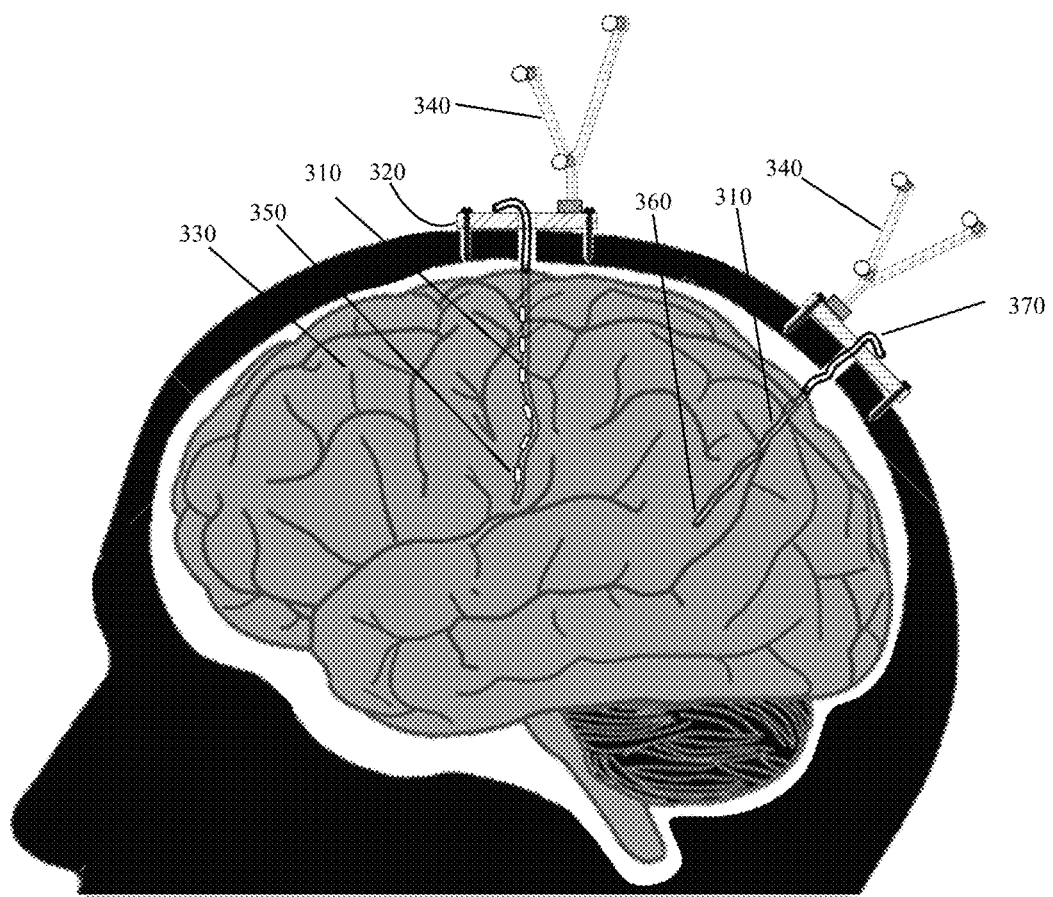
FIG. 3 illustrates an embodiment of a deformation sensor inserted in brain tissue during a medical procedure.

FIG. 3 illustrates an embodiment of a device for sensing deformation in tissue during an invasive procedure, such as brain surgery. A flexible fiber 310 such as wire is inserted through a rigid mount 320 into a tissue 330, here depicted as brain tissue. The rigid mount 320 is affixed to bone, in this embodiment the skull. Tracking markers 340 are attached to supporting arm structures (or branches) which are placed on the rigid mount 320. Generally a minimum of three tracking markers 340 is used to provide adequate tracking in 3D space, but four markers (or more) may be placed on the rigid mount 320 for increased accuracy. Alternatively, the location of the base of the fiber with respect to the brain can be tracked by using a tracked pointer tool to touch the point at which the flexible fiber exits the rigid mount.

The flexible fiber 310 has embedded sensors 350 along its length. The sensors 350 may include, for example, bend sensors, temperature sensors and/or strain sensors as disclosed in US201605468 (A1) entitled Tip Deformation Measuring Apparatus for Medical Procedures.

A distal end 360 of the flexible fiber 310 is located within the tissue 330, and the proximal end 370 of the flexible fiber remains outside of the tissue. The embedded sensors 350 of the flexible fiber 310 measure deformation of the tissue 330 during the surgical procedure, by measuring strain on the flexible fiber. For example, tissue deformation may occur due to opening the skull or introducing medical devices such as an access port. The tissue deformation causes a shift or bend of the flexible fiber 310 which is detected by the embedded sensors 350. The information from the sensors 350 may be relayed to the tracking system 112 and be incorporated with the resection evaluation application 216 to provide updated information regarding the conformation of the tissue 330 and location of the tissue to be resected.

Regarding the embedded sensors 350, a multiplicity of sensors or sensing materials are available that provide a feedback metric to a user of the deformation sensor device as disclosed herein. Examples of such sensors or sensing materials include but are not limited to Fiber Bragg Gratings (FBGs), electrical strain gauges, organic semiconductor strain gauges, photo-reactive substances (materials), thermally-reactive substances (materials), electrochromic substances (materials), radiochromic substances (materials), fiber optic channels, polarization maintaining optic fibers, photonic crystal fibers, EM receivers, and etc.

In addition each sensor or sensing material type may typically have its own preferred communication channel where applicable. For example Fiber Bragg Grating sensors need to be used in combination with optical fibers while electrical sensors may be connected through electrical wires, and organic strain gauges may be connected through a printed flexible circuit or have wireless communication channels. An electro chromic substance (material) may not even require a communication channel. It should be noted before continuing that Fiber Bragg gratings will be referred to as FBGs henceforth. The types of strain detectors that may be implemented are described further below and depicted in FIGS. 10 to 12.

Figure 4:
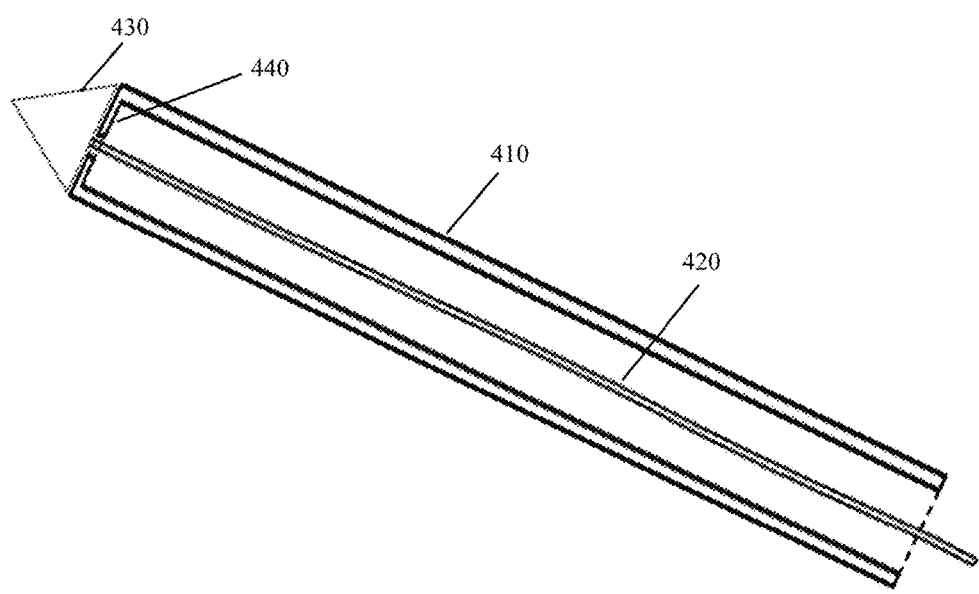
FIG. 4 illustrates an embodiment of a flexible fiber, a catheter and a tip of a deformation sensor.

FIG. 4 illustrates an embodiment of the deformation sensor device wherein a catheter 410 encloses a length of the flexible fiber 420 and a conical tip 430 is attached to the distal end of the flexible fiber. The catheter 410 assists in insertion of the flexible fiber 420 into the tissue 330 and, in the embodiment shown, has a shoulder 440 abutting the tip 430 so that as the catheter is inserted into the tissue, the tip is pushed ahead. The conical tip 430 also assists in the insertion of the flexible fiber 420 into the tissue 330 by virtue of its shape and may provide an anchor for the flexible fiber in the tissue once the flexible fiber is inserted into position.

Figure 5:
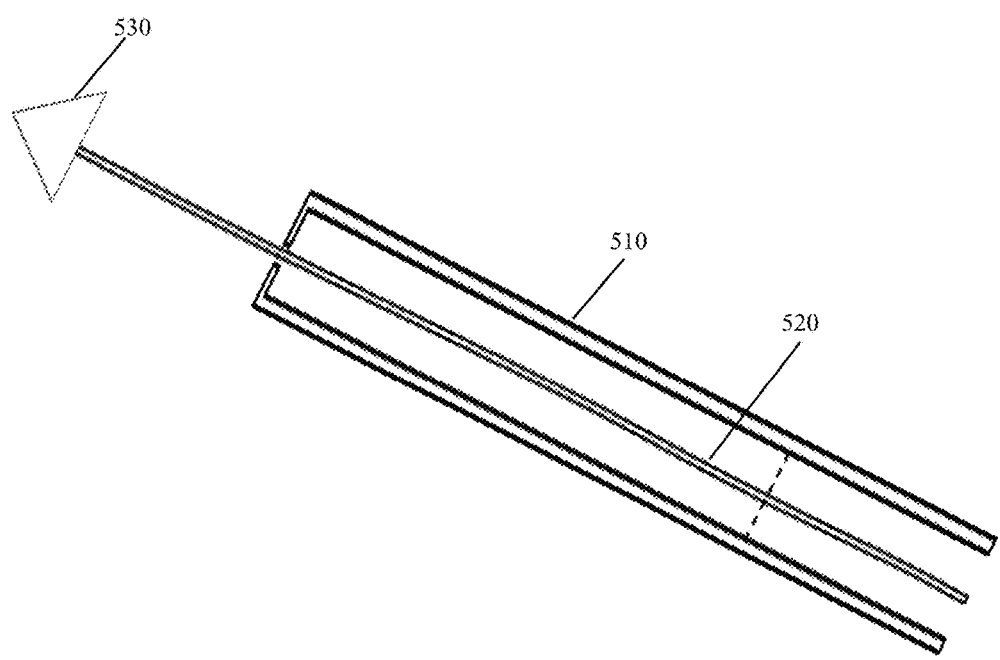
FIG. 5 illustrates a further embodiment of a flexible fiber, a catheter and a tip of d deformation sensor.

FIG. 5 illustrates the removal of the catheter 510 after the flexible fiber 520 has been positioned in the tissue. The catheter 510 is pulled out of the tissue, leaving the flexible fiber 520 in place in the tissue, anchored by the tip 530. The tip 530 may be made of a collagen or other dissolvable material, or may be an inflatable balloon to allow collapse and removal of the tip.

In an alternative embodiment, rather than employing a catheter 510 to insert the flexible fiber 520, the flexible fiber may be constructed with a memory metal, also referred to as shape memory alloy. The memory metal is rigid upon insertion of the flexible fiber 520, and slack once the flexible fiber is inserted in the tissue.

Figure 6:
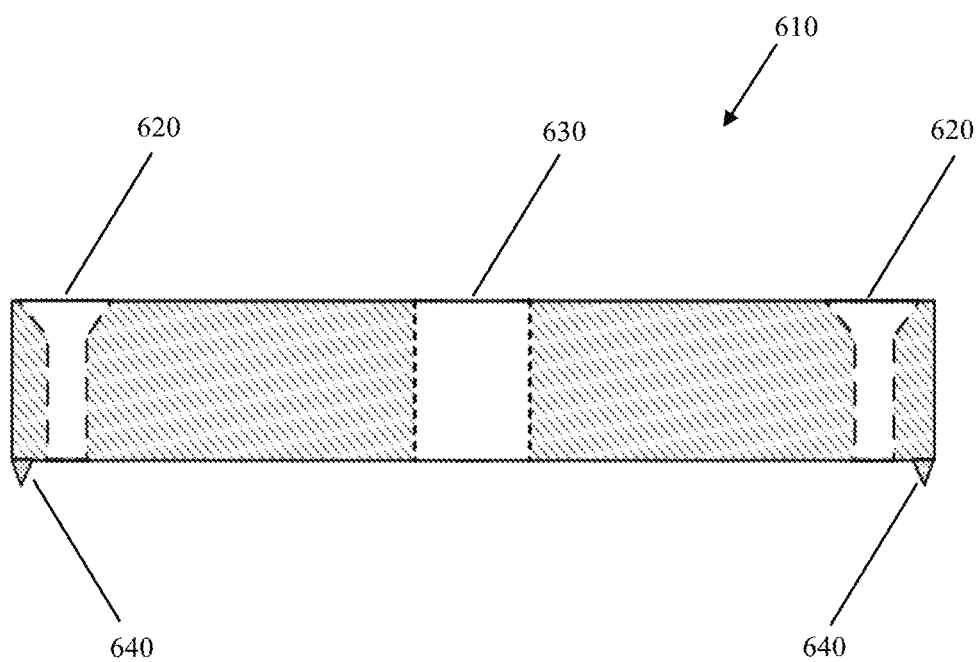
FIG. 6 illustrates an embodiment of a rigid mount of a deformation sensor.

FIG. 6 illustrates a rigid mount 610 for the deformation sensor device. The rigid mount 610 is affixed to a bone, such as the skull, overlying the tissue. The rigid mount 610 has one or more chamfered holes 620 for insertion of bone screws (not shown) to fix the rigid mount to bone and a transverse opening 630 for insertion of the flexible fiber into the tissue. The rigid mount 610 may also have spikes 640 on the side of the rigid mount abutting the bone to further secure the rigid mount onto the bone.

Figure 7:
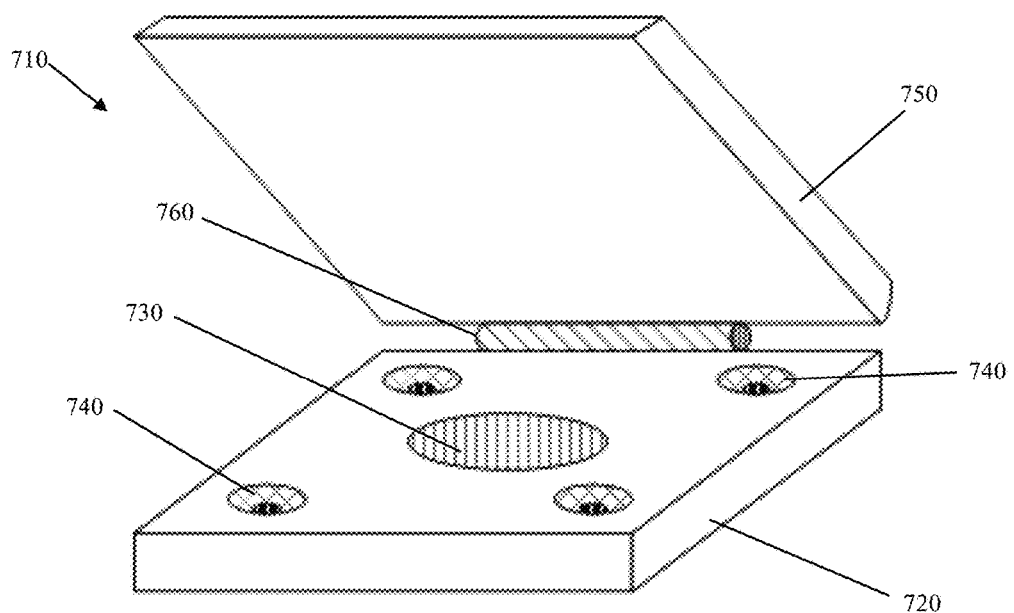
FIG. 7 illustrates a further embodiment of a rigid mount of a deformation sensor in an open configuration.

FIG. 7 illustrates another embodiment of a rigid mount 710, comprising a base 720 with a transverse opening 730 for the flexible fiber, holes for bone screws 740 and a cap 750 attached to the base 720 through a hinge 760 such as a living hinge. The rigid mount 710 is shown here in an open configuration, which allows insertion of the flexible fiber through the transverse opening 730 and into the tissue.

Figure 8:
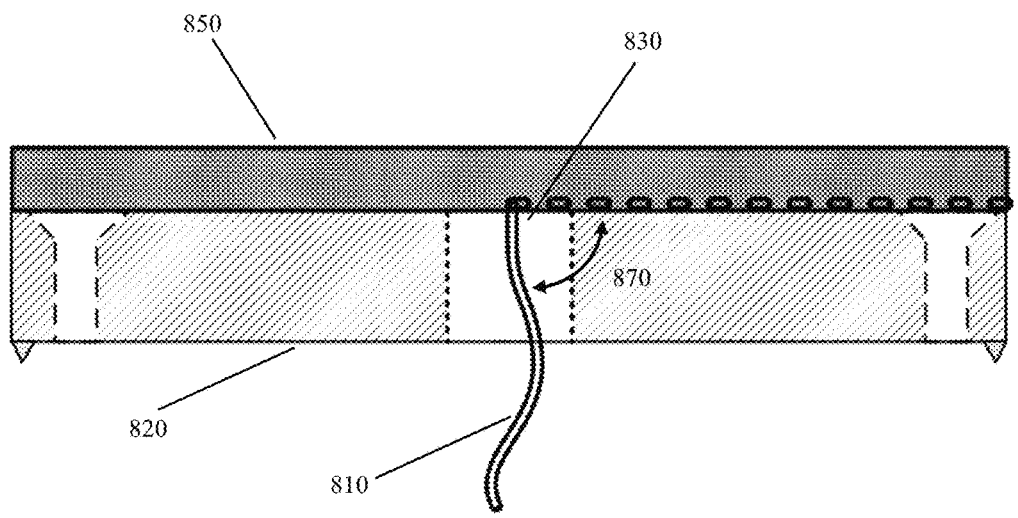
FIG. 8 illustrates a further embodiment of a rigid mount of a deformation sensor in a closed configuration.

As illustrated in FIG. 8, once the flexible fiber 810 is in position, the cap 850 can be closed against the base 820 holding the flexible fiber 810 in a fixed angle 870. The fixed angle 870, such as a 90 degree bend, located at the transverse opening 830 can be used as datum for position information to be transmitted to the navigation system.

Figure 9:
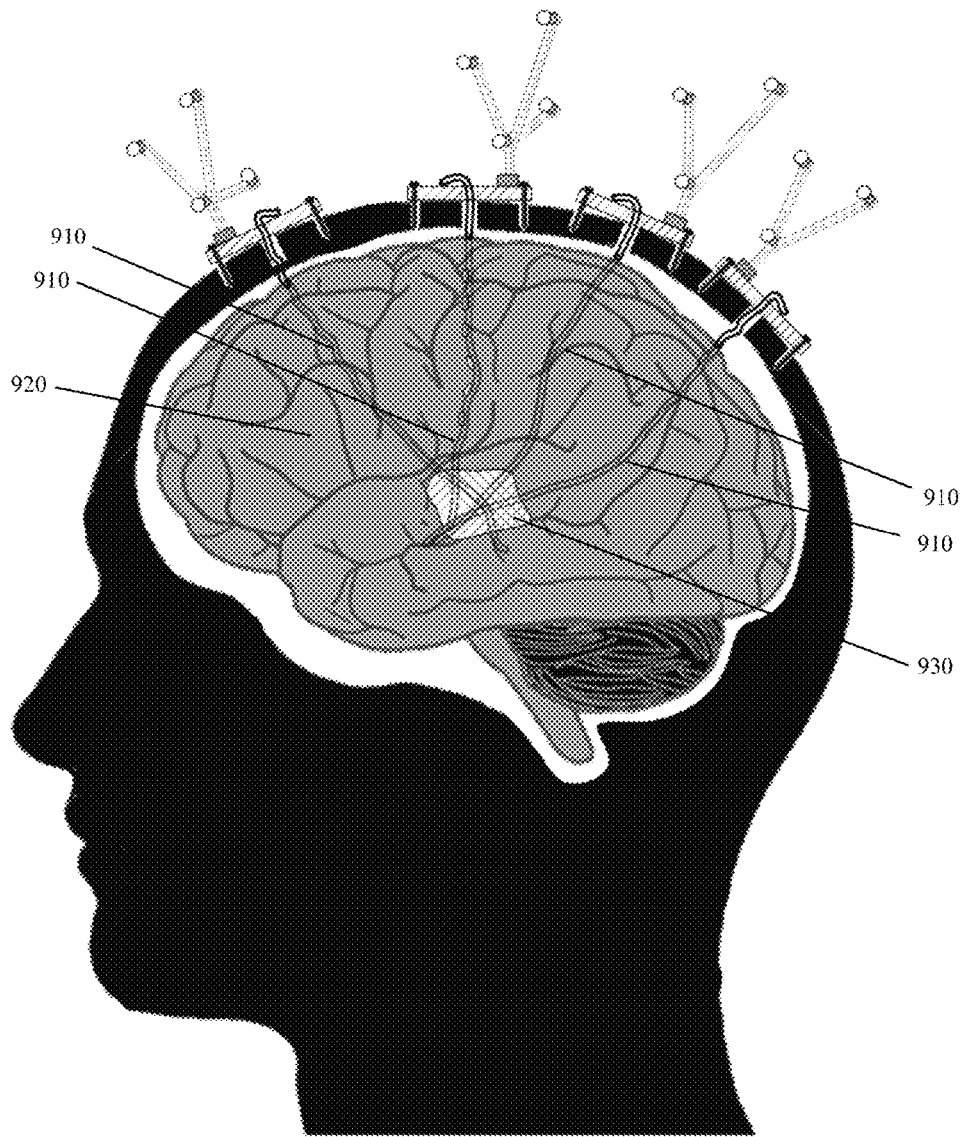
FIG. 9 illustrates an embodiment of employing a plurality of deformation sensors around a target tissue during a medical procedure.
Figure 10A:
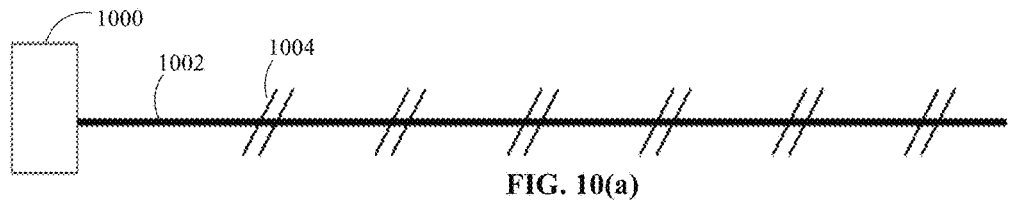
FIG. 10 (a) is a diagram showing a generic strain detection feedback system.
Figure 10B:
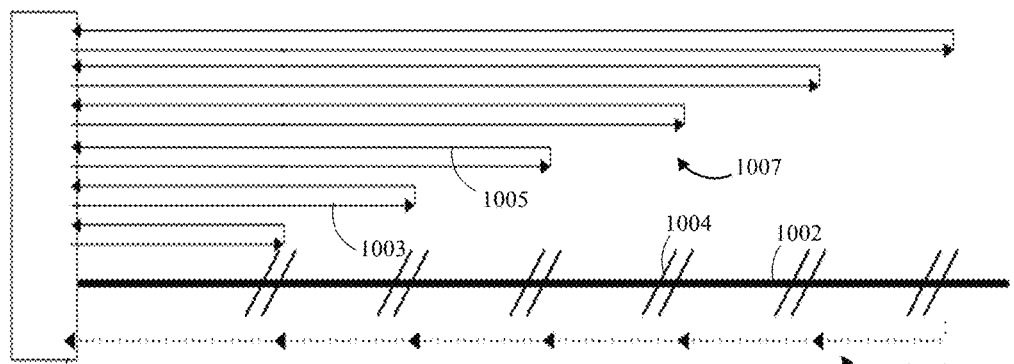
Figure 10C:
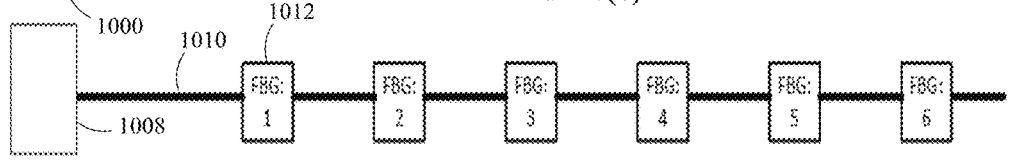
Figure 10D:
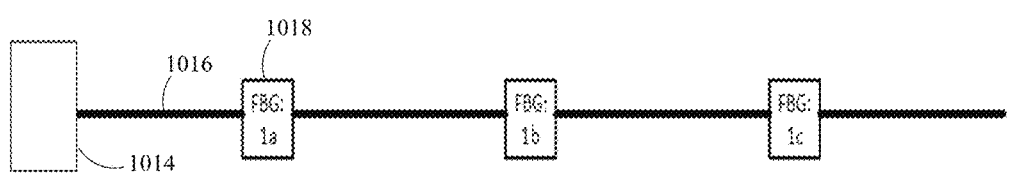
Figure 10E:
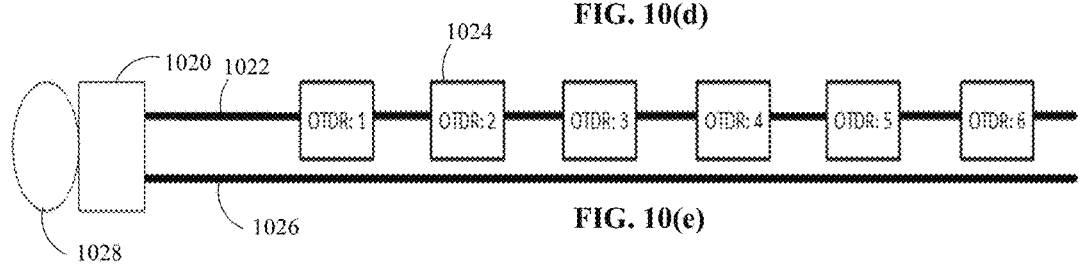

FIG. 9 illustrates employment of more than one deformation sensor device on a tissue such as brain during a medical procedure. The multiple flexible fibers 910 can be placed in the tissue 920 surrounding a target tissue 930 such as a tumor. The location information from the multiple flexible fibers 910 can thereby provide positional information for the tissue 920 and consequently a real-time assessment of the location of the target tissue 930. The multiple flexible fibers 910 may further assist in the surgical procedure by resisting movement and deformation of the tissue 920 in the region of the target tissue 930. Upon sensing deformation of the tissue 920, the flexible fibers 910 may resist the strain through electrical or mechanical means and thus counteract deformation of the tissue.

Types of Strain Detectors

Figure 11A:
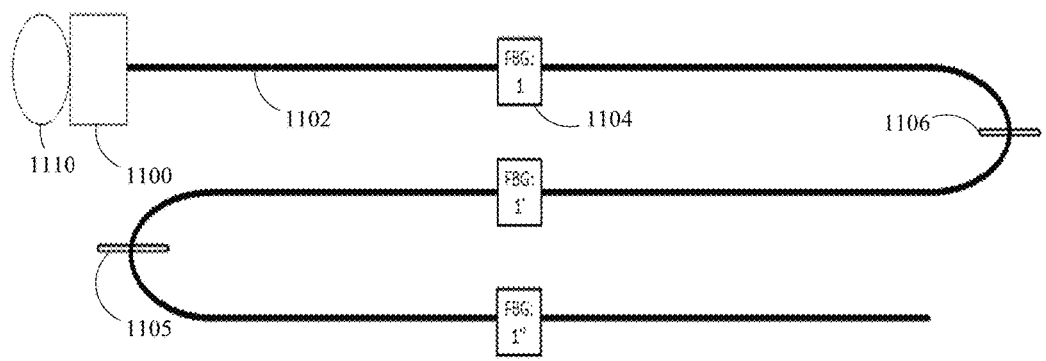
FIG. 11 (a) is a diagram showing a time division multiplexed strain detection feedback system.
Figure 11B:
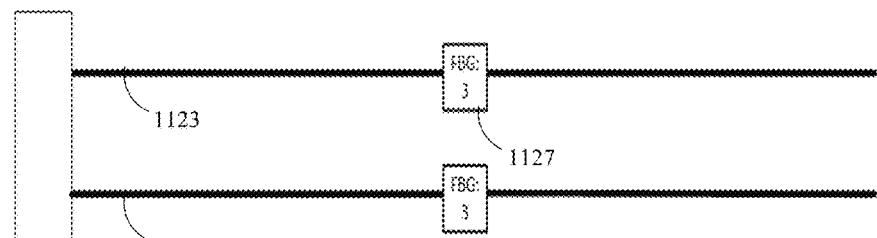
Figure 11C:
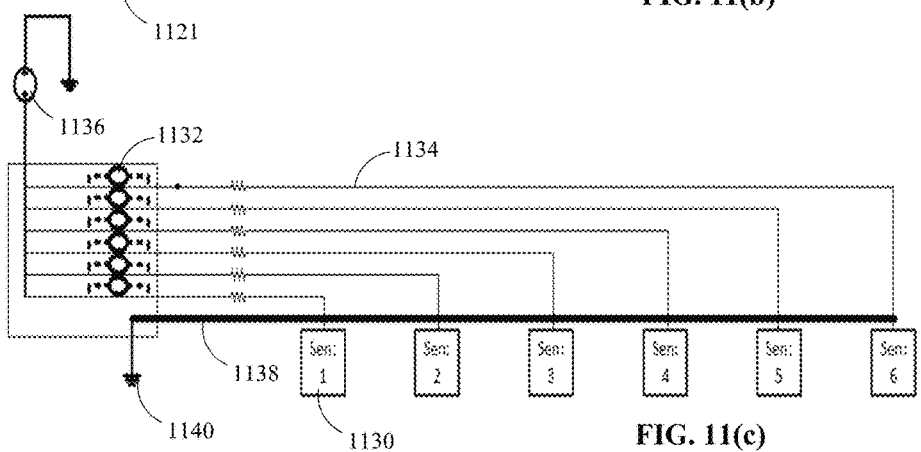

Variations of the embodiment described above and depicted in FIGS. 4 and 9 may be implemented using a multiplicity of strain detectors and detection mechanisms as depicted in FIGS. 10 and 11. These figures show block diagrams of strain detection feedback systems that may be implemented in the deformation sensor device as disclosed herein to allow the detection of strain at various locations on or in the tissue. It should be noted that any single implementation of a detection feedback system or combination of detection feedback systems thereof may be implemented for use as part of the device disclosed herein.

Generic Block Diagram of Strain Sensors

The first block diagram FIG. 10 (a) shows a generic strain detection feedback system that may be implemented in an embodiment of the device disclosed herein such as that depicted in FIGS. 4 and 9. It follows then that the communication channel 1102, strain sensors 1004, and detector/source 1000 of a generic strain detection feedback system may be embodied as a flexible fiber 310, embedded sensors 350, and an optical detector/optical source within the tracking system 112 respectively in the embodiment shown in FIG. 3. The optical detector/optical source may be attached to the rigid mount 320.

The diagram FIG. 10 (b) depicts the functioning of a generic strain detection feedback system. In such systems a signal is generally sent from the sensors to the detector to be analyzed against a reference. An example of this system is shown in the section 1009 of the diagram FIG. 10 (b). In the diagram the sensors 1004 send signals 1005 to the detector 1000. The detector then analyzes the signal 1005 and determines the strain on the particular sensors. In many embodiments these signals may be sent along the same communication channel such as 1002 or may be sent along separated channels or equivalently multiple separate wireless communication channels, or any combination thereof.

Commonly, strain detection feedback systems function by sending an energy signal from a detector/source 1000 which is returned to a detector after being altered (including reflecting the signal) in some way by a sensor 1004. The return signal is then analyzed in comparison to the initially sent signal or some reference to determine the amount of strain on a particular sensor. An example of this is shown at the top section 1007 of FIG. 10 (b). In this example the sent signals 1003 are being altered by the sensors 1004 depending on the strain applied to them and sent back as return signals 1005 to the detector/source 1000 along the communication channel 1002.

A light detector/source 1000 may emit an optical signal of variable bandwidth and wavelength which is partially or fully reflected, at the Bragg wavelength, in the form of an optical return signal by FBGs sensors 1004 to the optical detector/source 1000 where the signal is then analyzed to determine the amount of strain applied to the specific strain sensor. It should be noted that any light source and detector required in the embodiments of the deformation sensor device as disclosed herein may be in the form of a broadband, tunable band, or tunable wavelength source or detector and may be used in any combination thereof to meet the requirements of the strain detection feedback system as is known in the art.

The generic apparatus and generic principle function of strain detection feedback systems as shown in FIG. 10 (a) and FIG. 10 (b) have specific implementations reliant on the choice of hardware employed by the strain detection feedback system. However in order for a strain detection feedback system to uniquely locate its strain sensors positions and their respective strain magnitudes, the hardware typically is designed for integration with a complementary interrogation technique. There are many combinations of interrogation techniques and hardware which may be used to form a multitude of strain detection feedback systems which are well known to those skilled in the art.

Wavelength Division Multiplexing Using Fiber Bragg Gratings

The first strain detection feedback system to be described will be a wavelength division multiplexed system employing FBG strain sensors. This system may be considered as a further refinement of the embodiment described above in that it has the additional attribute of an interrogation technique. A block diagram of this embodiment is provided in FIG. 10 (c).

In this embodiment shown in FIG. 10 (c) the generic communication channel 1002, strain sensors 1004, and detector 1000 of the generic strain detection feedback system are embodied as a fiber optic communication channel 1010, FBGs 1012, and an optical detector/illumination source 1008 respectively.

This embodiment functions in a similar manner to the generic functioning of a strain detection feedback system depicted in FIG. 10 (b), wherein the sent signals 1003 are being altered by the sensors 1004 and sent back as return signals 1005 to the detector 1000 along the communication channel 1002. It follows then that the communication channel 1002, strain sensors 1004, detector 1000, signal 1003, and return signal 1005 of a generic strain detection feedback system are embodied as a fiber optic channel 1010, FBG strain sensors 1012, and optical detector 1008 FIG. 10 (c).

To ease explanation of the embodiment being described herein henceforth the term "reflection band" will refer to the range of all possible Bragg wavelengths an FBG may reflect incoming light back to the detector 1008, under the influence of any applied strain ranging from no applied strain ($\Delta_{BO}$) to the maximum strain, where the maximum strain may correspond to the level of strain which would cause the FBG to fracture, the level of strain at the maximum bending amount of the FBG, or an arbitrary predetermined imposed strain limit. In addition the term "original Bragg wavelength" will be used to refer to the Bragg wavelength of an FBG under no strain and the term "altered Bragg wavelength" will be used to refer to the Bragg wavelength of an FBG under an arbitrary level of applied strain.

The interrogation technique of wavelength division multiplexing is applied in this embodiment as shown in FIG. 10 (c) in order to differentiate which sensor 1012 (i.e. FBG: 1 . . . FBG: 6) a reflected input signal (return signal) 1005 is derived from and determine the magnitude of strain being applied at that specific FBG sensor 1012. In order to apply this technique the multiple FBG strain sensors 1012 labelled FBG: 1 . . . FBG: 6, must be located at various known locations along the length of the fiber optic cable 1010 and must have particular reflection bands. This technique works by segmenting the emission spectrum of the source into intervals (reflection bands) wherein each interval corresponds to a specific sensor. The segmentation is achieved by employing FBGs (FBG: 1 . . . FBG: 6) with original Bragg wavelengths ($\lambda_{BO-1}$ . . . $\lambda_{BO-6}$) such that the reflection band of that FBG sensor will not overlap with any other FBG sensors reflection band.

Once assigned a specific FBG sensor the following equation may be used to determine a strain value corresponding to the reflected input signal:

$$\varepsilon = \frac{\lambda_{BS} - \lambda_{BO}}{\lambda_{BO}(1 - P_e)} - \frac{(\alpha_\Lambda - \alpha_\eta)\Delta T}{(1 - P_e)}$$

where $\lambda_{BO}$ is the original Bragg wavelength of the assigned FBG sensor, $\lambda_{BS}$ is the wavelength of the reflected input signal and $\Delta T$ is the change in temperature at the FBG. The assigned FBG sensor along with this calculation then provides information as per the amount of applied strain and the location of that applied strain (i.e. a specific sensor 1012 (FBG: 1 . . . FBG: 6)) along the fiber optic channel containing the FBGs.

Intensity Division Multiplexing Using Fiber Bragg Gratings

The second strain detection feedback system to be described will be an Intensity division multiplexed system employing FBG strain sensors an example of which is disclosed in U.S. Pat. No. 6,879,742 entitled Using Intensity And Wavelength Division Multiplexing For Fiber Bragg Grating Sensor System. This system is similar to the embodiment described above in that it segments a detectable range (in this case the intensity of the reflected input signal) in order to determine which FBG sensor the reflected input signal was derived from. An exemplary block diagram of this embodiment is provided in FIG. 10 (d). It should be noted that the employed embodiment utilizes FBG sensors (FBG: 1a . . . FBG: 1c) having the same original Bragg wavelengths ($\lambda_{BO1}$) but differing in luminous reflectivity (i.e. percentage of signal at wavelength ($\lambda_{BO1}$) which is reflected).

The principle function of this second strain detection feedback system is identical to that of the first system above where the altered Bragg wavelength ($\lambda_{BS}$) is defined by the following equation $$\lambda_{BS} = \lambda_{BO}(1 - P_e)\varepsilon + \lambda_{BO}(\alpha_\Lambda - \alpha_\eta)\Delta T + \lambda_{BO}$$

Therefore the wavelength of the reflected signal ($\lambda_{BS}$) from the FBG may be compared to the Bragg wavelength of the FBG under no strain $\lambda_{BO}$ to determine the strain ($\varepsilon$) on the sensor 1018, given the temperature change is accounted for or held constant throughout.

In this embodiment shown in FIG. 10 (d) the generic communication channel 1002, strain sensors 1004, and detector 1000 of the generic strain detection feedback system are embodied as a fiber optic communication channel 1016, FBGs 1018, and an optical detector/illumination source 1014 respectively. This embodiment functions in a similar manner to the generic functioning of a strain detection feedback system depicted in FIG. 10 (b), where the sent signals 1003 are being altered by the sensors 1004 and sent back as return signals 1005 to the detector 1000 along the communication channel 1002.

To ease explanation of the embodiment being described herein, henceforth the term "intensity band" will refer to the range of all possible luminous intensities (within a tolerance or not) an FBG may reflect incoming light at, back to the detector 1008. This "intensity band" will likely be centered on the reflectivity value of the particular FBG wherein the likelihood of an input signal being reflected at a particular luminous intensity may be normally distributed around this reflectivity value as the mean.

The interrogation technique of intensity division multiplexing is applied in the embodiment being described herein as shown in FIG. 10 (d) in order to differentiate which sensor 1018 (i.e. FBG: 1a . . . FBG: 1c) a reflected input signal (return signal) is derived from and determine the magnitude of strain being applied at that specific sensor 1018. In order to apply this technique the multiple FBG strain sensors 1018 labelled FBG: 1a . . . FBG: 1c, must be located at various known locations along the length of the fiber optic cable 1010 and must have specific intensity bands. This technique works by segmenting the intensity detection range into intervals wherein each interval corresponds to a specific sensor. The segmentation is achieved by employing FBGs (FBG: 1a . . . FBG: 1c) with different reflectivity values.

The wavelength of the reflected input signal will be the altered Bragg wavelength of the FBG sensor. The detector 1014 may then analyze this reflected input signal to determine its wavelength (or range of wavelengths). Following this determination the intensity range may be used to assign the reflected input signal to a specific FBG sensor (FBG: 1a . . . FBG: 1c) depending on which intensity band the wavelength of the reflected input signal falls within. Once assigned a specific FBG sensor the following equation may be used to determine a strain value corresponding to the reflected input signal:

$$\varepsilon = \frac{\lambda_{BS} - \lambda_{BO}}{\lambda_{BO}(1-P_e)} - \frac{(\alpha_\Lambda - \alpha_\eta)\Delta T}{(1-P_e)}$$

where $\lambda_{go}$ is the original Bragg wavelength of the assigned FBG sensor, $\lambda_{BS}$ is the wavelength of the reflected input signal and $\Delta T$ is the change in temperature at the FBG. The assigned FBG sensor along with this calculation then provides information as per the magnitude of applied strain and the location of that applied strain (i.e. a specific sensor 1018).

Time Division Multiplexing Using Fiber Bragg Gratings

The fourth strain detection feedback system to be described will be a time division multiplexed system employing FBG strain sensors. This system is similar to the embodiments described above in that it segments a detectable range (in this case the time of arrival of the reflected input signal) in order to determine which FBG sensor the reflected input signal was derived from. An exemplary block diagram of this embodiment is provided in FIG. 11 (*a*). It should be noted that the employed embodiment utilizes FBG sensors (FBG: 1, FBG: 1', FBG: 1") having the same original Bragg wavelengths ($\lambda_{BO1}$) and the same reflectivities (i.e. percentage of signal at wavelength ($\lambda_{BO1}$) which is reflected). The reflectivity of the FBGs in this case must be divided amongst the FBGs such that the percentages accumulate to a maximum of 100% so that the luminous intensity is enough such that it reaches the last sensor with enough luminous intensity to produce a return signal detectable by the detector 1100.

The principle function of this fourth strain detection feedback system is identical to that of the first system above where the altered Bragg wavelength ($\lambda_{BS}$) is defined by the following equation $$\lambda_{BS} = \lambda_{BO}(1-P_e)\varepsilon + \lambda_{BO}(\alpha_\Lambda - \alpha_\eta)\Delta T + \lambda_{BO}$$

Therefore the wavelength of the reflected signal ($\lambda_{BS}$) from the FBG may be compared to the Bragg wavelength of the FBG under no strain $\lambda_{BO}$ to determine the strain ($\varepsilon$) on the sensor 1104, given the temperature change is accounted for or held constant throughout.

In this embodiment shown in FIG. 11 (*a*) the generic communication channel 1002, strain sensors 1004, and detector 1000 of the generic strain detection feedback system shown in FIG. 10 (*a*) are embodied as a fiber optic communication channel 1102, FBGs 1104, and an optical detector 1100 and illumination source 1110 respectively.

This embodiment functions in a similar manner to the generic functioning of a strain detection feedback system depicted in FIG. 10 (*b*), where the sent signals 1003 are being altered by the sensors 1004 and sent back as return signals 1005 to the detector 1000 along the communication channel 1002. It follows then that the communication channel 1002, strain sensors 1004, detector 1000, signal 1003, and return signal 1005 of a generic strain detection feedback system are embodied as a fiber optic channel 1102, FBG strain sensors 1104, optical detector 1100, optical input signal and reflected input signals respectively in the system shown in FIG. 11 (*a*).

To ease explanation of the embodiment being described herein henceforth the term "time range" will refer to the interval of time in which all possible reflected input signals by a particular FBG 1104 may return to the detector 1100 (with or without an error tolerance). This "time range" may be centered on the mean time it would take the initial signal to return to the detector after emission by the source 1110 with upper and lower limits defined by a confidence interval. Wherein it is known to a predetermined confidence, such as a 95%, that the time it takes from initial emission for a signal to be reflected by a specific sensor and return to the detector is in the time interval bounded by these limits.

The interrogation technique of time division multiplexing may be applied in the deformation sensor device embodiment as described herein and shown in FIG. 11 (*a*) in order to differentiate which FBG sensor 1104 (i.e. FBG: 1, FBG: 1', and FBG: 1") a reflected input signal (return signal) is derived from and determine the magnitude of strain being applied at that specific sensor 1104. In order to apply this technique the multiple FBG strain sensors 1104 labelled FBG: 1, FBG: 1', and FBG: 1", must be located at various known locations along the length of the fiber optic cable 1102 and must have specific time ranges. This technique works by segmenting the temporal detection range into intervals wherein each interval corresponds to a specific sensor. The segmentation is achieved by placing the FBGs along the fiber optic channel 1102 at specific distances such that the time of flight measurements (amount of time it takes for a signal to travel from the source to the specific FBG and travel back) detectably differ. For example, there may be 3 time ranges, each one corresponding to a particular FBG sensor 1104 (FBG: 1, FBG: 1', and FBG: 1"). The intervals between the time ranges are the intervals of time after initial emission of a signal at which a reflected input signal may return to the detector after being reflected by a specific FBG 1104. The wavelength of this reflected input signal will be the altered Bragg wavelength of the specific FBG sensor. The detector 1100 may then analyze this reflected input signal to determine its wavelength (or range of wavelengths). Following this determination the time interval may be used to assign the reflected input signal to a specific FBG sensor (FBG: 1, FBG: 1', or FBG: 1") depending on which time range the reflected input signal returns within.

Once assigned a specific FBG sensor the following equation may be used to determine a strain value corresponding to the reflected input signal.

$$\varepsilon = \frac{\lambda_{BS} - \lambda_{BO}}{\lambda_{BO}(1-P_e)} - \frac{(\alpha_\Lambda - \alpha_\eta)\Delta T}{(1-P_e)}$$

Where $\lambda_{go}$ is the original Bragg wavelength of the assigned FBG sensor, $\lambda_{BS}$ is the wavelength of the reflected input signal and $\Delta T$ is the change in temperature at the FBG. The assigned FBG sensor along with this calculation then provides information as per the amount of applied strain and the location of that applied strain (i.e. a specific sensor 1104 (FIG. 11 (*a*))) along the fiber optic channel.

Spatial Division Multiplexing Using Fiber Bragg Gratings

The fourth strain detection feedback system to be described will be a spatial division multiplexed system employing FBG strain sensors. An exemplary block diagram of this embodiment is provided in FIG. 11 (*b*). It should be noted that the employed embodiment utilizes FBG sensors having the same original Bragg wavelengths ($\lambda_{BO1}$) and the same reflectivity's (i.e. percentage of signal at wavelength ($\lambda_{BO1}$) which is reflected). In this embodiment however there are two communication channels used to differentiate between the FBG sensors.

The principle function of this fourth strain detection feedback system is identical to that of the first system above where the altered Bragg wavelength ($\lambda_{BS}$) is defined by the following equation:

$$\lambda_{BS} = \lambda_{BO}(1-P_e)\varepsilon + \lambda_{BO}(\alpha_\Lambda - \alpha_\eta)\Delta T + \lambda_{BO}$$

Therefore the wavelength of the reflected signal ($\lambda_{BS}$) from the FBG may be compared to the Bragg wavelength of the FBG under no strain $\lambda_{BO}$ to determine the strain ($\varepsilon$) on the sensor 1127 (FIG. 11 (*b*)), given the temperature change is accounted for or held constant throughout. In this embodiment shown in FIG. 11 (*a*) the generic communication channel 1002, strain sensors 1004, and detector 1000 of the generic strain detection feedback system shown in FIG. 10 (*a*) are embodied as two fiber optic communication channels 1123 and 1125, FBGs 1127, and an optical detector/illumination source 1121 respectively.

This embodiment functions in a similar manner to the generic functioning of a strain detection feedback system depicted in FIG. 11 (*b*), where the sent signals 1003 are being altered by the sensors 1004 and sent back as return signals 1005 to the detector 1000 along the communication channel 1002. It follows then that the communication channel 1002, strain sensors 1004, detector 1000, signal 1003, and return signal 1005 of a generic strain detection feedback system are embodied as a fiber optic channels 1125 and 1127, FBG strain sensors 1127, optical detector 1121, a generic optical input signal, and a generic reflected input signal respectively in the system shown in FIG. 11 (*b*).

The interrogation technique of spatial division multiplexing is applied in the embodiment being described herein as shown in FIG. 11 (*b*) in order to differentiate which FBG sensor 1127 a reflected input signal (return signal) is derived from and determine the magnitude of strain being applied at that specific sensor 1127. In order to apply this technique, the two FBG strain sensors 1127 labelled FBG: 3, must be located at various known locations along the length of separate fiber optic channels 1123 and 1127.

In order to apply this technique (i.e. excluding other multiplexing techniques) with N FBG sensors the system would need to employ n=N fiber optic channels. This technique works by identifying which fiber optic channel the reflected input signal is coming from and once known the specific FBG that corresponds to that channel. Determining which fiber optic channel the signal is coming from may be achieved by employing a separate source and detector for each fiber optic channel and connecting the detectors output to a microcontroller programmed to differentiate between the inputs and calculate the strain based on the signals as follows. It should be noted that many optical detectors such as the ones described above are designed using microcontrollers and thus the microcontroller mentioned herein may be superfluous to the separate detectors and the two may be interfaced without an external microcontroller. The wavelength of this reflected input signal will be the altered Bragg wavelength of the FBG sensor. The detector 1121 may then analyze this reflected input signal to determine its wavelength (or range of wavelengths). Following this determination the fiber optic channel of the reflected input signal may be used to assign the reflected input signal to a specific FBG sensor depending on which fiber optic channel the reflected input signal was received from. Once assigned a specific FBG sensor, the following equation may be used to determine a strain value corresponding to the reflected input signal:

$$\varepsilon = \frac{\lambda_{BS} - \lambda_{BO}}{\lambda_{BO}(1 - P_e)} - \frac{(\alpha_\Lambda - \alpha_\eta)\Delta T}{(1 - P_e)}$$

where $\lambda_{go}$ is the original Bragg wavelength of the assigned FBG sensor, $\lambda_{BS}$ is the wavelength of the reflected input signal and $\Delta T$ is the change in temperature at the FBG. The assigned FBG sensor along with this calculation then provides information as per the amount of applied strain and the location of that applied strain (i.e. a specific sensor 1127).

Optical Time Domain Reflectometry in Fiber Optic Channels

In addition to FBG based strain detection feedback systems there exists other forms of optical strain detection feedback systems that may be used to detect strain or faults within a fiber optic channel. A common example of such a system is an Optical Time Domain Reflectometry system which will be referred to as OTDR henceforth. Two exemplary OTDR system set ups are shown in FIG. 10 (*e*). The basic set up of such a system is to have a signal source 1028 and detector 1020 attached to the fiber optic channel (1022 or 1026) to be monitored.

The bottom channel 1026 shown in the figure represents a basic OTDR system. An OTDR system functions by injecting a fiber optic channel with an optical signal pulse and measuring the optical signal which is reflected back to the point of injection at discreet time points until the injected signal reaches the end of the channel. Using time of flight calculations and knowing the speed of light in the channel the return signals are then correlated to a specific distance along the channel where they originated essentially creating a signal trace of distance along channel vs. signal.

An example of such a signal trace is described here. In general the injected signal is reflected back to the detector as a result of two types of phenomena, the first being Rayleigh backscattering and the second being Fresnel reflection. Rayleigh backscattering results from the injected signal interacting with impurities (also termed dopants) in the fiber optic cable and scattering in all directions, wherein the signal picked up by the detector is the portion of the scattered signal which was oriented back towards detector. Rayleigh backscattering occurs consistently along the length of the fiber optic cable, additionally the magnitude of interaction is more or less proportional to the strength of the signal at the point (distance along the fiber optic cable) of interaction. With no other phenomenon affecting the injected signal the signal trace should resemble a downward sloping line proportional to the loss in injected signal strength as a result of the continuous Rayleigh backscattering interactions along the length of the fiber optic cable.

In order to employ a basic OTDR system in the deformation sensor device as disclosed herein, a comparison of an initial signal trace against a signal trace taken after insertion of the flexible fiber into the tissue may be acquired. By subtracting the two traces by using a computer for example any differences will be revealed and may be analyzed to infer if any significant changes to the fiber optic channel such as the ones described above may have potentially occurred. In addition, the magnitude of strain or other force that may have caused such a change may also be determinable given the relative difference of signals at distances along the comparison signal trace.

An alternative strain detection feedback system which employs an OTDR detector and sensor interprets the bend loss in optical fibers to determine the bending angle or equivalent, of the fiber from its initial position. Such a system is depicted in FIG. 10 (*e*) along the fiber optic channel 1022. This system employs a built-in displacement sensor to more accurately measure the strain at specific sensor locations along the length of the channel. To do so the system uses pairs of fiber optic channel integrated mirrors to provide a relative change in the signal strength over an interval of fiber optic channel. The relative change may then be compared to a known table to quantify the amount of bending the channel incurs between the mirrors.

The principle function of this strain detection feedback system will be further elaborated with reference to FIG. 10 (e) along the fiber optic channel 1022. Each OTDR sensor 1024 shown in FIG. 10 (e) is formed of two fiber optic channel integrated mirrors designed to reflect a percentage of the luminous intensity of an input signal injected at one end of the fiber back to the point of injection. The mirror closest to the source 1028 that injects the signal is termed the reference mirror and will provide the reference signal and the mirror further from the source will be termed the sensor mirror and will provide the sensing signal. Both mirrors are designed to reflect the same luminous intensity. The mirrors are oriented around an interval of fiber optic channel that will define the region where the acquired bending angle or equivalent information of the sensor will refer to. The bending angle of the interval is dependent on the relative value of the reflected signals by both the reference and sensing mirrors according to the equation provided as follows:

$$\text{Normalized OTDR Signal} = C\left\{\left(\frac{V_r - V_s}{V_r}\right)_i - \left(\frac{V_r - V_s}{V_r}\right)_o\right\}$$

where C is a proportionality constant $$\left(\frac{V_r - V_s}{V_r}\right)_i$$

is the normalized ratio at some time i after the starting ratio $$\left(\frac{V_r - V_s}{V_r}\right)_o$$

is taken at time o. The values depicted with $V_r$ and $V_s$ are the induced detector outputs in arbitrary units by the reflected signals at the detector 1020 by the reference and sensor mirrors respectively of the sensor 1024. The normalized ratios are used to offset the natural reduction in signal at successive distances along the optical fiber channel resulting from Rayleigh Backscattering and other sources of signal loss. The Normalized OTDR Signal, as calculated above, is dependent on the rotation angle of the interval of fiber optic channel contained within the sensor 1024. This strain detection feedback system may be employed in an embodiment of the deformation sensor device disclosed herein wherein the bending of the fiber optic channels would be indicative of the amount of strain that those fibers may have been exposed to.

In this embodiment shown in FIG. 10 (e) the generic communication channel 1002, strain sensors 1004, and detector 1000 of the generic strain detection feedback system shown in FIG. 10 (a) are embodied as the fiber optic communication channels 1022 and 1026, displacement sensors 1024, and an optical detector 1020 and illumination source 1028 respectively.

This embodiment functions in a similar manner to the generic functioning of a strain detection feedback system depicted in FIG. 10 (b) where the sent signals 1003 are being altered by the sensors 1004 and sent back as return signals 1005 to the detector 1000 along the communication channel 1002. It follows then that the communication channel 1002, strain sensors 1004, detector 1000, signal 1003, and return signal 1005 of a generic strain detection feedback system are embodied as a fiber optic channels 1022 and 1026, displacement sensors 1024, optical detector 1020, optical source 1028, an optical input signal, and a reflected input signal respectively in the system shown in FIG. 10 (e).

Electrical Strain Detection Feedback Systems

In addition to optical fiber based strain detection feedback systems there exists other forms of strain detection feedback systems that may be used to detect strain or faults within a tissue phantom. A common example of such a system is an electrical circuit based system such as the system depicted in FIG. 11 (c). Two exemplary electrical systems may employ simple ammeter sensors or bonded strain gauge sensors. FIG. 11 (c) shows a generic circuit diagram of an electrical strain detection feedback system as it may be employed in an embodiment of the device as disclosed herein. In general an electrical strain detection feedback system will have a voltage source 1136 to power the circuit, electrical communication channels 1134 to relay information from the sensors 1130, detectors (such as a computer or microcontroller) 1132 to interpret an acquired electrical signal from the sensors along the electrical communication channel, and a relative ground 1140 as is required for all circuits to function.

In the first exemplary system the sensors 1130 are simply connection points at which the communication channels 1134 connect to the ground 1140 of the circuit. When the connections exist current flows from the voltage source 1136 to the ground 1140 through the communication channels 1134. The detector 1132 is an array of ammeters measuring the current flow through each communication channel 1134 and are connected to a computer or microcontroller programmed with instructions to provide an indication of which communication channel has an error if any of the communication channel currents drop to zero while the voltage source 1136 is on. Thus if a connection is broken, for example through the application of excess strain, the microcontroller will provide information as to which sensor was damaged.

It should be noted that all of the electrical communication channels may be oriented along a single electrical cable with a single ground wire or along individual electrical communication channel cables each with their own ground. If the location of the sensors are known along the length of the electrical communication channel then when an indication is provided that an error has occurred along that channel the location of which channel has been damaged will indicate where excess strain was applied. However if the current of a group of successive electrical communication channels drops to zero and the channels are oriented in a single cable than it may be probabilistically assumed that the channel that the connection that broke was that of the sensor closest to the detectors 1132 when the system is oriented in the manner shown in FIG. 11 (c). This results from the sensors 1130 being essentially in a serial orientation thus if a lower connection is broken all of the higher connections will be broken as well. This particular embodiment although useful provides no information as to the magnitude of the strain being applied at the point of interest.

The alternate electrical strain detection feedback system embodiment may use electrical bonded strain gauge sensors in place of the connection based sensors as described above. Bonded strain gauges take advantage of the inherent relationship between the resistance of an electrical conductor and the strain being applied to it. As the bonded strain gauge is exposed to compression or tension along its long axis the electrical conductor increases and decreases in length effectively changing its resistance.

The change in voltage caused by the change in resistance may then be measured and correlated with the change in strain. This embodiment is also illustrated in FIG. 11 (c), the only difference being this embodiment would not require the ammeters 1132 hence why they are shown with dashed lines, indicating they are removable. When being used to illustrate this embodiment the sensors 1130 in FIG. 11 (c) may be any circuits employing strain gauges utilized in the form of a sensor to output the strain felt at the location of the sensor. Two strain gauges may be employed, one located on the wire while the other is used to compensate for any temperature-related strain response. As strain is detected by the strain gauge on the wire, the voltage change caused by the increased or decreased resistance of the electrical strain gauge may be measured by a voltmeter and output to a microcontroller (not shown). This output may then be converted to a strain reading by the equation provided below and be communicated to the user:

$$\varepsilon = \frac{4v}{BV \cdot GF}$$

where $\varepsilon$ is the strain, v is the voltage read across the bridge of the circuit by the voltmeter, BV is the bridge excitation voltage provided by the source 1136, and GF is the gage factor. This voltage source 1136 and ground 1140 may also be common across all sensors (SEN: 1 . . . SEN: 6) in the strain detection feedback system shown in FIG. 11 (c).

Combination of Strain Detection Feedback Systems

In addition to the embodiments of strain detection feedback systems described above, any combination of strain detection feedback systems may be employed to improve the effective capability of any individual systems. Two examples of such embodiments are provided in FIG. 12. The first block diagram FIG. 12 (a) shows an FBG based strain detection feedback system employing wavelength division and time division multiplexing. This system functions in the same manner as a time division multiplexed system where in addition to interrogating the reflected input signal for which time range it falls within it is also interrogated for what wavelength band it falls within (this may require the use of an external computer or microcontroller). The wavelength of this reflected input signal will be the altered Bragg wavelength of the FBG sensor. The detector may then analyze this reflected input signal to determine its wavelength (or range of wavelengths). Following this determination the time range may be used to assign the reflected input signal to a specific FBG sensor group (FBG: Xa, FBG: Xb, FBG: Xc). Following determination of the sensor group the specific sensor in the group (i.e. FBG: 1y . . . FBG: 6y) may be determined by the wavelength band the reflected input signal falls in. Once assigned a specific FBG sensor (FBG: 1a . . . FBG: 6c) the following equation may be used to determine a strain value corresponding to the reflected input signal:

$$\varepsilon = \frac{\lambda_{BS} - \lambda_{BO}}{\lambda_{BO}(1 - P_e)} - \frac{(\alpha_\Lambda - \alpha_\eta)\Delta T}{(1 - P_e)}$$

where $\lambda_{BO}$ is the original Bragg wavelength of the assigned FBG sensor, $\lambda_{BS}$ is the wavelength of the reflected input signal and $\Delta T$ is the change in temperature at the FBG. The assigned FBG sensor along with this calculation then provides information as per the amount of applied strain and the location of that applied strain (i.e. a specific sensor 1104).

Figure 12A:
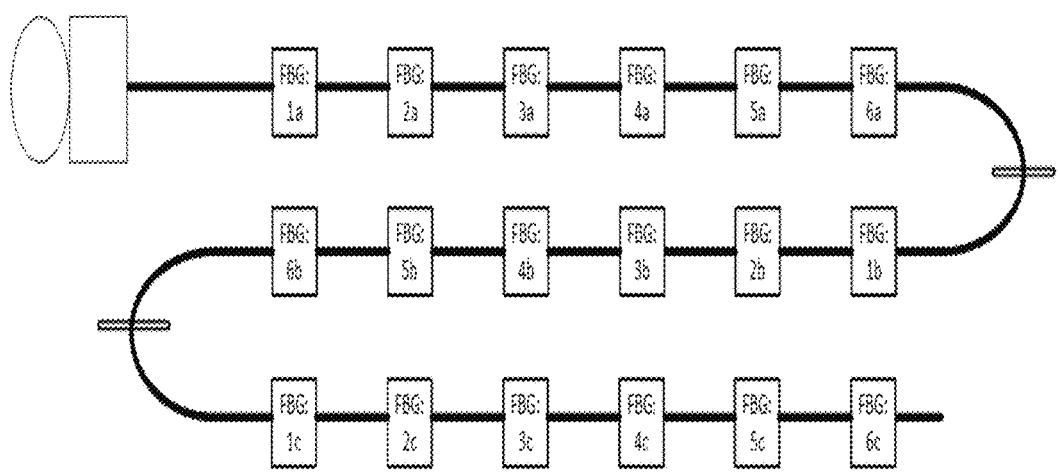
FIG. 12 (a) is an illustration of a combined multiplexing system of fiber Bragg grating sensors.
Figure 12B:
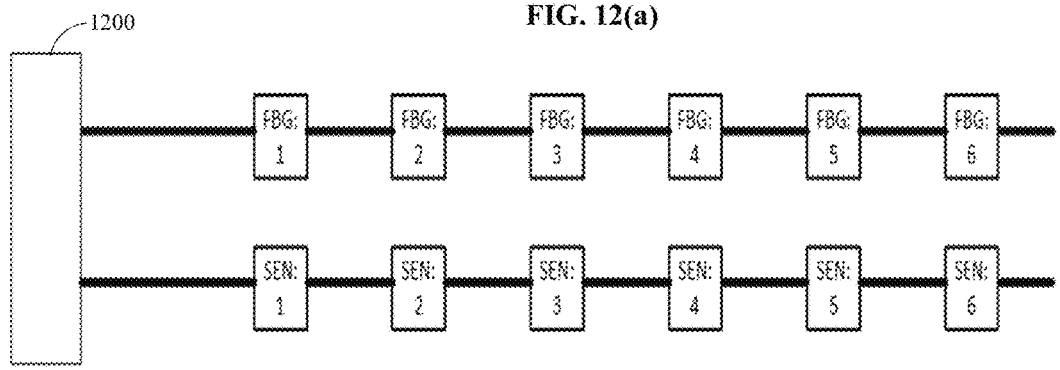

The second block diagram FIG. 12 (b) shows a combination of an electrical, wavelength, and spatial division multiplexed strain detection feedback systems. To further clarify the block diagram shows an FBG based wavelength division multiplexed system spatially multiplexed with an electrical based strain detection feedback system. These individual systems work with the same principles used above where the spatial division multiplexing is used to combine the two other strain detection feedback systems with a single detector (which may be formed of multiple microcontrollers or computers). This system is simply an aggregation of parts with a common detector 1200 used to spatially multiplex the parts as opposed to the embodiment shown in FIG. 12 (a) which is a composition of systems. Regardless of this differentiation, either combination may be used to improve the functioning of such strain detection feedback systems.

It should be noted that any of the sensors 1004 of the strain detection feedback systems as described may also be implemented with wireless communication channels (i.e. communication channel 1002 may be wireless) where possible as opposed to the non-wireless communication channels as described.

Method

The deformation sensing device is used for invasive medical procedures to measure tissue deformation in the area of a surgery. An example of a method for use of the deformation sensing device is described here.

Prior to or during a surgical procedure, one or more flexible fibers with embedded sensors are inserted into tissue in the region of a target tissue, such as a tumor. To insert the flexible fibers, a rigid mount is affixed to bone, for example to the skull. The rigid mount can be affixed by bone screws as well as by spikes extending from the rigid mount. The location of the rigid mount is measured, for example by using attached tracking markers or by touching a tracked pointer tool to the base of the flexible fiber where it exits the rigid mount.

The flexible fiber is guided through a transverse hole in the rigid mount, through the bone and into the soft tissue. Guidance of the flexible fiber through the soft tissue can be aided using a catheter, or the flexible fiber can be constructed with memory metal that is rigid upon insertion and flexible once it is in position. The flexible fiber can also have a conical or inflatable tip to assist in penetrating the tissue, and which can also be used to anchor the flexible fiber once it is in position. The tip can be eliminated following surgery by using a collagen or other dissolvable material, or by deflating an inflatable tip.

Once one or more flexible fibers are placed in the tissue, the sensor locations are determined by a strain detection system, as described above, wherein a detector receives a signal from the sensor which is used to measure strain, which may be used to calculate the location of the sensor. An imposed bend in the flexible fiber at the point where it traverses the rigid mount may also be used as location datum to calculate the location of the sensors. As surgery proceeds, changes in strain and location of the sensors can be used to measure the tissue deformation and resultant change in the location of the target tissue. Further, a multitude of flexible fibers can be inserted around the area of the target tissue and if increased strain is measured, it can be counteracted by the flexible fibers.

Measurements of the sensor location may be relayed to the navigation system, which can integrate the information with prior imaging data of the tissue, thereby predicting and accommodating for movement of the target tissue.

We claim:

1. A deformation sensing device for sensing and counteracting a tissue deformation in a medical procedure, comprising:
    a plurality of flexible fibers, each flexible fiber of the plurality of flexible fibers having a proximal end and a distal end, for counteracting the tissue deformation by resisting movement and deformation of the tissue in a region of a target tissue, and each flexible fiber resisting strain in at least one manner of an electrical manner and a mechanical manner;
    at least one sensor embedded in each flexible fiber of the plurality of flexible fibers for measuring the strain in each flexible fiber;
    a tracking system comprising a detector and an optical navigation system, the optical navigation system comprising a camera and a computing device;
    a plurality of rigid mounts operable in relation to the plurality of flexible fibers for affixing to a bone, each rigid mount of the plurality of rigid mounts having a transverse opening for facilitating respectively inserting each flexible fiber therethrough and into the tissue, the plurality of rigid mounts having a corresponding plurality of locations measurable by the tracking system; and
    an insertion mechanism, comprising a memory metal, for inserting each flexible fiber through each transverse opening into the tissue,
    the detector configured to receive information from the at least one sensor, the information incorporable with a resection evaluation application related to the medical procedure, and
    the optical navigation system configured to receive the information from the detector for calculating, using the computing device, at least one location of the at least one sensor and the tissue deformation by using the at least one location of the at least one sensor and any change in the at least one location during the medical procedure, and
    the computing device configured to update information regarding conformation of the tissue and a location of the target tissue,
    whereby the tissue deformation is counteracted.

2. The device as in claim 1, further comprising a plurality of retractable tips, each retractable tip of the plurality of retractable tips attached to the distal end of each of the flexible fibers.

3. The device as in claim 2, wherein each retractable tip comprises an inflatable balloon.

4. The device as in claim 2, wherein each retractable tip comprises at least one of a collagen and a soluble material.

5. The device as in claim 2, wherein each retractable tip of the plurality of retractable tips comprises at least one of: an inflatable balloon; a collagen; and a soluble material.

6. The device as in claim 1, wherein the at least one sensor comprises at least one strain gauge.

7. The device as in claim 6, wherein the at least one sensor further comprises at least one of: at least one temperature sensor and at least one pressure sensor.

8. The device as in claim 1, wherein the at least one strain sensor comprises at least one of an organic electronics sensor and an optical fiber Bragg-grating.

9. The device as in claim 1, wherein the insertion mechanism further comprises a catheter reversibly enclosing a length of each flexible fiber.

10. The device as in claim 1, wherein the memory metal is rigid upon insertion and slack when inserted into the tissue.

11. The device as in claim 1, wherein each rigid mount of the plurality of rigid mounts comprises at least one chamfered opening for reversibly affixing each rigid mount of the plurality of rigid mounts to the bone with at least one bone screw.

12. The device as in claim 1, wherein the tracking system further comprises a tracking array attached to each rigid mount of the plurality of rigid mounts.

13. The device as in claim 12,
    wherein the tracking system is configured to locate a plurality of markers in a plurality of images captured by the camera and to determine spatial positions of the plurality of markers, and
    wherein the tracking array comprises at least one of: a plurality of passive spheres and at least one active LED.

14. The device as in claim 1, wherein each rigid mount comprises: a base with the transverse opening; and a cap attached to the base with a hinge.

15. The device as in claim 1, wherein the at least one sensor comprises at least one of a temperature sensor and a pressure sensor.

16. The device as in claim 1, wherein each flexible fiber of the plurality of flexible fibers further comprises at least one shape memory alloy for counteracting at least one of electrical strain and mechanical strain.

* * * * *